United States Patent
Dudek et al.

(10) Patent No.: US 11,020,035 B2
(45) Date of Patent: Jun. 1, 2021

(54) SELF-CONTAINED EEG RECORDING SYSTEM

(71) Applicant: Epitel, Inc., Salt Lake City, UT (US)

(72) Inventors: Francis E. Dudek, Salt Lake City, UT (US); Michael K. Elwood, Farmington, UT (US); John H. Fischer, Cottonwood Heights, UT (US); Mark J. Lehmkuhle, Salt Lake City, UT (US); Jean M. Wheeler, Salt Lake City, UT (US)

(73) Assignee: Epitel, Inc., Salt Lake City, UT (US)

( * ) Notice: Subject to any disclaimer, the term of this patent is extended or adjusted under 35 U.S.C. 154(b) by 502 days.

(21) Appl. No.: 15/421,085

(22) Filed: Jan. 31, 2017

(65) Prior Publication Data

US 2017/0215759 A1    Aug. 3, 2017

Related U.S. Application Data

(60) Provisional application No. 62/289,837, filed on Feb. 1, 2016.

(51) Int. Cl.
*A61B 5/291* (2021.01)
*A61B 5/316* (2021.01)
(Continued)

(52) U.S. Cl.
CPC ............ *A61B 5/291* (2021.01); *A61B 5/0006* (2013.01); *A61B 5/316* (2021.01); *A61B 5/6814* (2013.01);
(Continued)

(58) Field of Classification Search
CPC ... A61B 5/0476; A61B 5/0478; A61B 5/0408; A61B 5/0492; A61B 5/4094;
(Continued)

(56) References Cited

U.S. PATENT DOCUMENTS 4,936,306 A  *  6/1990  Doty .................... A61B 5/0478
                                                600/373
5,483,967 A     1/1996  Ohtake
(Continued)

FOREIGN PATENT DOCUMENTS

JP      2010527709 A    8/2010
WO   WO2015055156 A1   4/2015

OTHER PUBLICATIONS

International Searching Authority/US; International Search Report and Written Opinion; International Application No. PCT/US2017/016024 dated Apr. 20, 2017.
(Continued)

*Primary Examiner* — Eun Hwa Kim
(74) *Attorney, Agent, or Firm* — Cafardi, Ferguson, Wyrick, Weis & Gabriel, LLC; Andrew M. Gabriel

(57) ABSTRACT

Disclosed systems include a self-contained electroencephalogram (EEG) recording patch comprising a first electrode, a second electrode and wherein the first and second electrodes cooperate to measure a skin-electrode impedance, a substrate containing circuitry for generating an EEG signal from the measured skin-electrode impedance, amplifying the EEG signal, digitizing the EEG signal, and retrievably storing the EGG signal. The patch also comprises a power source and an enclosure that houses the substrate, the power source, and the first and second electrodes in a unitary package.

5 Claims, 11 Drawing Sheets

(51) Int. Cl.
   *A61B 5/00* (2006.01)
   *A61B 17/34* (2006.01)

(52) U.S. Cl.
   CPC .......... *A61B 5/742* (2013.01); *A61B 17/3468* (2013.01); *A61B 5/4094* (2013.01); *A61B 5/6833* (2013.01); *A61B 5/746* (2013.01); *A61B 2560/0209* (2013.01); *A61B 2560/0412* (2013.01); *A61B 2560/0431* (2013.01); *A61B 2562/164* (2013.01)

(58) Field of Classification Search
   CPC ... A61B 5/6814; A61B 5/6839; A61B 5/6832; A61B 5/6833
   See application file for complete search history.

(56) References Cited

U.S. PATENT DOCUMENTS

| | | | |
|---|---|---|---|
| 5,755,230 | A | 5/1998 | Schmidt et al. |
| 6,117,077 | A | 9/2000 | Del Mar et al. |
| 7,885,706 | B2* | 2/2011 | Ludvig .............. A61B 5/04004 600/382 |
| 7,970,450 | B2 | 6/2011 | Kroecker et al. |
| 8,626,261 | B2 | 1/2014 | Ko et al. |
| 8,805,527 | B2 | 8/2014 | Mumford et al. |
| 8,818,481 | B2* | 8/2014 | Bly .................... A61B 5/0205 600/391 |
| 9,186,083 | B2 | 11/2015 | Osvath |
| 9,241,649 | B2* | 1/2016 | Kumar ................ A61B 5/6833 |
| 2002/0188216 | A1 | 12/2002 | Kayyali et al. |
| 2007/0249952 | A1 | 10/2007 | Rubin et al. |
| 2007/0270678 | A1 | 11/2007 | Fadem et al. |
| 2008/0082019 | A1 | 4/2008 | Ludving et al. |
| 2008/0091090 | A1* | 4/2008 | Guillory .............. A61B 5/0478 600/301 |
| 2008/0243022 | A1* | 10/2008 | Donnett .............. A61B 5/0476 600/544 |
| 2008/0294031 | A1* | 11/2008 | Wilson ................ A61B 5/0408 600/383 |
| 2012/0035451 | A1* | 2/2012 | Jaffe .................... A61B 5/0408 600/373 |
| 2012/0179062 | A1 | 7/2012 | Wilson |
| 2012/0209102 | A1 | 8/2012 | Ylotalo et al. |
| 2012/0330125 | A1 | 12/2012 | Wilson et al. |
| 2013/0310676 | A1 | 11/2013 | Jung |
| 2014/0051044 | A1* | 2/2014 | Badower .............. A61B 5/0478 434/236 |
| 2014/0121557 | A1* | 5/2014 | Gannon ................ A61B 5/002 600/549 |
| 2014/0206975 | A1* | 7/2014 | Lang .................. A61B 5/04001 600/391 |
| 2015/0038870 | A1* | 2/2015 | Yoo .................... A61B 5/0476 600/544 |
| 2015/0351690 | A1 | 12/2015 | Toth et al. |
| 2015/0374255 | A1* | 12/2015 | Vasapollo ............ A61B 5/0478 600/301 |
| 2016/0029958 | A1* | 2/2016 | Le ...................... A61B 5/6835 600/383 |
| 2016/0089049 | A1* | 3/2016 | Hung .................... A61B 5/333 600/391 |
| 2016/0256111 | A1* | 9/2016 | Cheng .................. A61B 5/0002 |
| 2016/0374583 | A1* | 12/2016 | Cerruti ................ A61B 5/6833 600/301 |
| 2017/0095176 | A1* | 4/2017 | Sun ...................... A61B 5/7225 |
| 2020/0229706 | A1* | 7/2020 | Nishimura ............ A61B 5/274 |

OTHER PUBLICATIONS

Intellectual Property Office of Australia; Examination Report; Australian Patent Application No. 2017215192; dated Nov. 22, 2018.
Japanese Patent Office; Office Action for Application No. 2018-559672 dated Aug. 27, 2019.
European Patent Office; Extended European Search Report; European Patent Application No. 17748065.4; dated Aug. 22, 2019.

* cited by examiner

SELF-CONTAINED EEG RECORDING SYSTEM

CROSS-REFERENCE TO RELATED APPLICATIONS

This application, under 35 U.S.C. § 119, claims the benefit of U.S. Provisional Patent Application Ser. No. 62/289,837 filed on Feb. 1, 2016, and entitled "Self-contained EEG Recording System," the contents of which are hereby incorporated by reference herein.

FIELD OF THE DISCLOSURE

The present disclosure relates to a self-contained electro-encephalogram (EEG) recording device. In particular, some disclosed embodiments allow for monitoring EEG seizure activity from the scalp. Further disclosed embodiments may also allow recording epochs of EEG from the scalp.

BACKGROUND

The disclosures of each and every reference noted within this disclosure are hereby fully incorporated herein by reference.

There is a present need for an EEG recording system that is self-contained as one unit, is as small as possible, is simple by reducing the complexity of analyzing data on the device, and relatively water tight. In such cases where the desired EEG recording is for seizures, or determining sleep quality, it is not necessary to analyze the recorded data in real time, thus simplifying the need for increased processing power on the device. Many existing EEG recording systems, such as U.S. Pat. No. 8,688,209 and U.S. Pat. App. Pub. No. 2008/0091090, are concerned with analyzing the data for spikes or seizures in real time and displaying that data, or some indication of that data, on a display attached to the device.

The majority of sleep staging devices are incorporated as part of masks such as those in U.S. Pat. Nos. 7,848,794 and 8,204,584, or without masks that are attached to the scalp with a harness, such as those in U.S. Pat. App. Pub. No. 2011/0098593, or a head band and removable data acquisition box such as those in WO/2010/107928, and operate with multiple modes, such as those in U.S. Pat. No. 8,870,764. These devices are typically used in whole, or in part, to help diagnose obstructive sleep apnea (OSA), and tend to have multiple connections such as those in U.S. Pat. App. Pub. No. 2008/0319277. They can also be configured to provide feedback to the user as a means to optimize sleep such as those in U.S. Pat. No. 8,628,462.

Other physiological monitoring devices require multiple hinged "wings" containing electrodes separate from a central body, such as those in U.S. Pat. No. 8,538,503, or are designed to be reusable/recoverable such as those in U.S. Pat. App. Pub. No. 2014/0206977. The above-described limitations and drawbacks of existing systems may be disadvantageous or undesirable as would be appreciated by those of skill in the art. Other drawbacks and disadvantages of existing systems also exist.

SUMMARY

Accordingly, the disclosed systems and methods address the drawbacks and disadvantages of existing systems.

Accordingly disclosed systems include a self-contained electroencephalogram (EEG) recording patch comprising a first electrode, a second electrode and wherein the first and second electrodes cooperate to measure a skin-electrode impedance, a substrate containing circuitry for sensing an EEG signal from the skin-electrode impedance, amplifying the EEG signal, digitizing the EEG signal, and retrievably storing the EEG signal. The patch also comprises a power source and an enclosure that houses the substrate, the power source, and the first and second electrodes in a unitary package.

Further disclosed embodiments may comprise an indicator that indicates an active and an inactive state of the patch. In some embodiments, the indicator further comprises an LED. In still further embodiments, the indicator further comprises an audible tone generator.

In some embodiments, the substrate containing circuitry further comprises circuitry for electromechanical activation of the patch. In some embodiments, the circuitry for electromechanical activation of the patch further comprises at least one switch. In some embodiments, the circuitry for electromechanical activation of the patch further comprises at least one Hall-effect sensor.

In some embodiments, the self-contained EEG recording patch may comprise a third electrode. In some embodiments, the enclosure comprises a substantially waterproof polymer. In some embodiments, the first electrode and the second electrode further comprise memory shape alloy electrodes, and plungers to inject the memory shape alloy electrodes into a scalp and mechanically fix the patch thereto.

Further disclosed embodiments include a seizure alerting system comprising a self-contained EEG recording patch comprising a first electrode, a second electrode, wherein the first and second electrodes cooperate to measure a skin-electrode impedance, a substrate containing circuitry for sensing an EEG signal from the skin-electrode impedance, amplifying the EEG signal, digitizing the EEG signal, and retrievably storing the EEG signal. The EEG patch also comprises a power source, a transmitter for transmitting the EEG signal, and an enclosure that houses the substrate, the power source, the transmitter, and the first and second electrodes in a unitary package. The alerting system further comprises a base station that receives the transmitted EEG signal, monitors the EEG signal for an indication of a seizure, and signals an alert when a seizure is indicated.

In some embodiments, the seizure alerting system further comprises a remote alerting device capable of communicating with the base station that signals an alert when the base station signals an alert. In some embodiments, remote alerting device comprises a smartphone.

Other embodiments of the patch may include fabrication of electrodes on printed circuit boards separate from the circuit board or substrate. These electrode printed circuit boards are then attached to the main circuit board or substrate using standard surface mount reflow electronics assembly techniques. This provides an advantage by eliminating the requirement for exotic and expensive metal surface finishes (that are typically required on most electrodes) when fabricating the circuit board or substrate. These electrode printed circuit boards are referred to herein as a "dais boards" and the method of fabrication is referred to herein as "dais assembly." The surface finish of the electrode on printed circuit boards may be selective gold, immersion silver, carbon, or other materials suitable as a biopotential electrode interface. Other embodiments are also possible.

Other disclosed embodiments include a biopotential recording system comprising a first dais board comprising a first electrode, a second dais board comprising a second electrode, and wherein the first and second electrodes sense a voltage, a substrate containing circuitry for generating an EEG signal from the voltage, amplifying the EEG signal, digitizing the EEG signal, and retrievably storing the EGG signal. The biopotential recording system also comprises a power source and an enclosure that houses the substrate, the power source, and the dais board in a unitary package.

In some embodiments, the biopotential recording system further comprises an indicator that indicates an active and an inactive state of the system. In some embodiments, the indicator further comprises an LED or an audible tone generator.

In some embodiments, the substrate containing circuitry further comprises circuitry for electromechanical activation of the system. In some embodiments, the circuitry for electromechanical activation of the system further comprises at least one switch or at least one Hall-effect sensor. Other embodiments are also possible.

Figure 1:
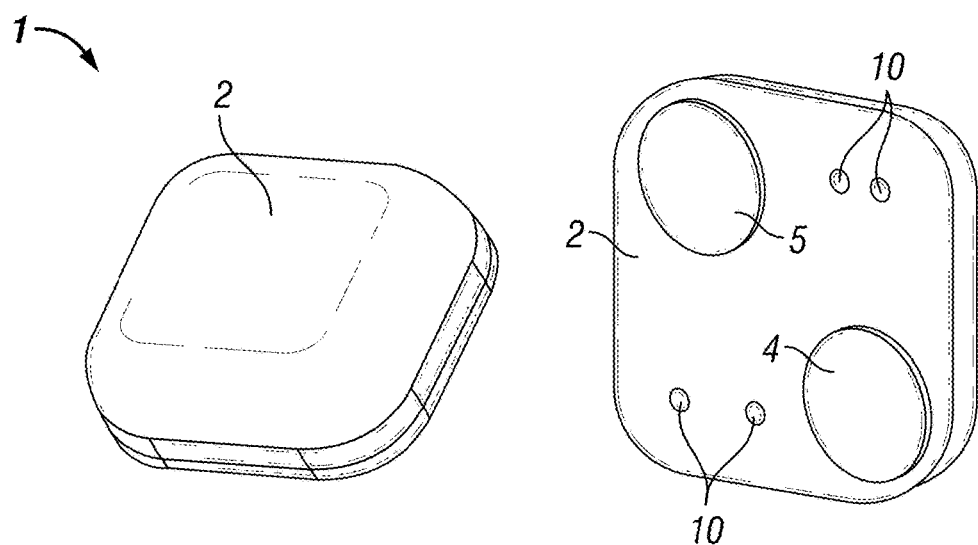
FIG. 1 is a perspective top view and bottom view illustration of an embodiment of a self-contained EEG recording patch as a seizure counting tool in accordance with the disclosure.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope of the invention as defined by the appended claims.

DETAILED DESCRIPTION

FIG. 1 is a perspective top view and bottom view illustration of an embodiment of a self-contained EEG recording patch 1 as a seizure counting tool in accordance with the disclosure. As shown in the top view (left side of FIG. 1), the patch 1 is self-contained in an enclosure 2. In some embodiments, the enclosure 2 may be formed of a plastic, polymer, composite, or the like that is water-resistant, waterproof, or the like.

For the embodiment of FIG. 1, the enclosure 2 contains all of the electronics for recording EEG from at least two electrodes 4, 5. The electrodes 4, 5, are on the bottom, or scalp facing, side shown on the right side of FIG. 1. Also included on the bottom, or scalp facing, side are pins, or other interface, for I/O programming and data retrieval 10.

In some embodiments, enclosure 2 may house a circuit board or substrate 20, which provides connections for electrodes 4, 5, and optionally 6 (for 3-electrode embodiments), amplification circuitry 7, data processor 8, storage 9, one or more switches 15 to activate/inactivate the recording state, one or more indicators 12 of the recording state, a power source 11, I/O programming and data retrieval 10. Electrodes 4, 5, 6 may be formed of any suitable material. For example, electrodes 4, 5, 6 may comprise gold, silver, silver-silver chloride, carbon, combinations of the foregoing, or the like. As noted above, the entire patch 1 may be self-contained in a watertight enclosure 2. In the some embodiments, the patch 1 is designed to be a self-contained EEG machine that is one-time limited use per user and disposable.

In the FIG. 1 embodiment, the self-contained patch 1 has two electrodes 4, 5 and is used as a discrete, single-channel tool to count seizures. In most instances it is desirable, but not necessary, that the user has had a previous diagnosis of a seizure disorder using traditional wired EEG based on the 10-20 montage using the bipolar derivation. This diagnosis provides clinical guidance as to the most optimal location to place the self-contained patch 1 for recording electrographic seizure activity in an individual user. The electrode 4, 5 spacing uses a bipolar derivation to form a single channel.

The self-contained patch 1 can be placed anywhere on the scalp of a patient to record EEG. Ideally, the patch 1 may be packaged such that removal from the package activates the circuitry. This may be accomplished by the packaging having electromechanical activation, such as a magnetic component that, when removed, eliminates a magnetic field around the patch. In the absence of the magnetic field, magnetic field-sensitive components 17 within the patch, such as Reed- and Hall-effect type elements, may be configured to bring the patch out of a sleep-state and into a record-state. In some embodiments, the self-contained patch 1 may also include an indicator 12 of the change in recording state from record to sleep and from sleep to record. For example, the indicator 12 may be an LED element 13 that flashes to indicate the change in state, or the indicator 12 may also include an auditory signaler 14 to indicate the change in state. Other indicators 12, or combinations of indicators 12, are also possible.

Embodiments of the patch 1 can be placed anywhere on the scalp as placing a conventional wired EEG electrode. The patch 1 self-adheres to the scalp either through a conductive adhesive, an adhesive with a conductive, and/or through mechanical means such as intradermal fixation with a memory-shape metal, or the like.

Once attached to the scalp, some embodiments enable the patch 1 to perform as a single-channel seizure detection device. In this embodiment, the patch 1 records a single channel of differential EEG continuously, uninterrupted for up to seven days. Following a recording session, the patch 1 may be placed in the mail and returned to a service that reads the EEG to identify epileptiform activity according to ACNS guidelines. In other embodiments, data may be retrieved from the patch 1 via I/O data retrieval port 10 and uploaded or otherwise sent to a service for reading the EEG data. I/O data retrieval port 10 may operate with any suitable I/O protocol, such as USB protocol, Bluetooth protocol, or the like. Epileptiform activity such as seizures and interictal spikes may be identified in a report along with EEG recording attributes and made available to physicians through a user's electronic medical records, or the like.

In another embodiment, the self-contained patch 1 may also employ capacitive coupling, such as is disclosed in U.S. Pat. App. Pub. 2010/0222686, as a means to "spot-check" signal quality. In this embodiment, a handheld, or other device, is brought near the patch 1 to capacitively couple with the device as a means to interrogate the EEG or impedance signal in real time.

In another embodiment, the self-contained patch 1 may be used to alert to seizures in real time, or near real time. In this embodiment the patch 1 may continuously transmit to a base station 21 that runs seizure detection algorithm(s) in real-time. The base station 21 may sound an alarm if a seizure is detected either at the base station 21 itself, or through communication to other devices 22 capable of providing a visual and/or audio and/or tactile alarm. The base station 21 may also keep a record of EEG for later review by an epileptologist. These EEG may also be archived in electronic medical records, or otherwise stored.

In another embodiment, the self-contained patch 1 could be used to record ultra-low frequency events from the scalp such as cortical spreading depressions. In this embodiment, the amplifier circuitry 7 may be appropriate for recording DC signals. Alternatively, the amplifier circuitry 7 may be appropriate for recording both DC and AC signals. The patch 1 in this embodiment may be used after a suspected stroke event as a means to monitor for the presence or absence of cortical spreading depressions and/or seizures or other epileptiform activity. The patch 1 in this embodiment may be placed on the scalp of a patient by any type of health care provider such as an emergency medical technician, medical doctor, nurse, or the like.

In yet another embodiment, the patch 1 may employ capacitive coupling, such as that disclosed in U.S. Pat. App. Pub. 2010/0222686, to monitor for cortical spreading depressions in real time. In this embodiment, the spreading depressions could be analyzed over time and displayed as a visualization of the EEG. The patch 1 may store these EEG (e.g., in storage 9) for later retrieval. These EEG could also be archived in electronic medical records, or the like.

Figure 2:
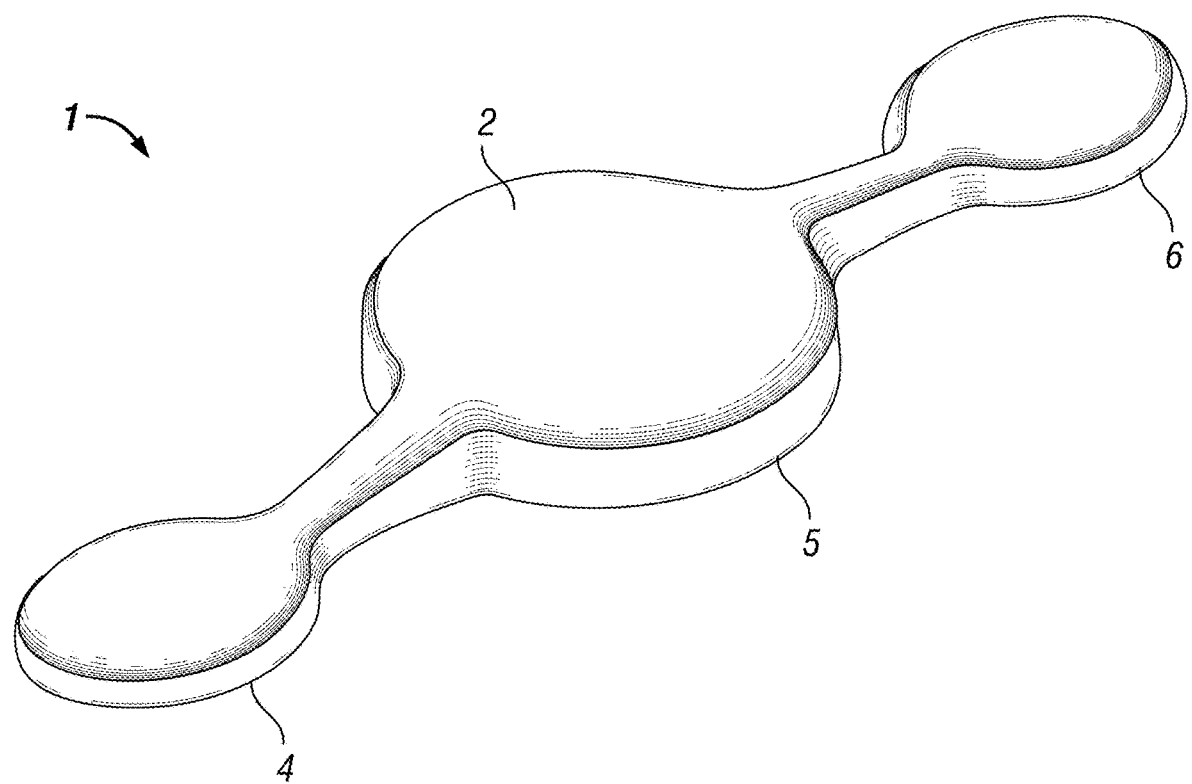
FIG. 2 is a perspective top view of an illustration of an embodiment of a self-contained EEG recording patch for recording frontal EEG below the hairline in accordance with the disclosure.
Figure 3:
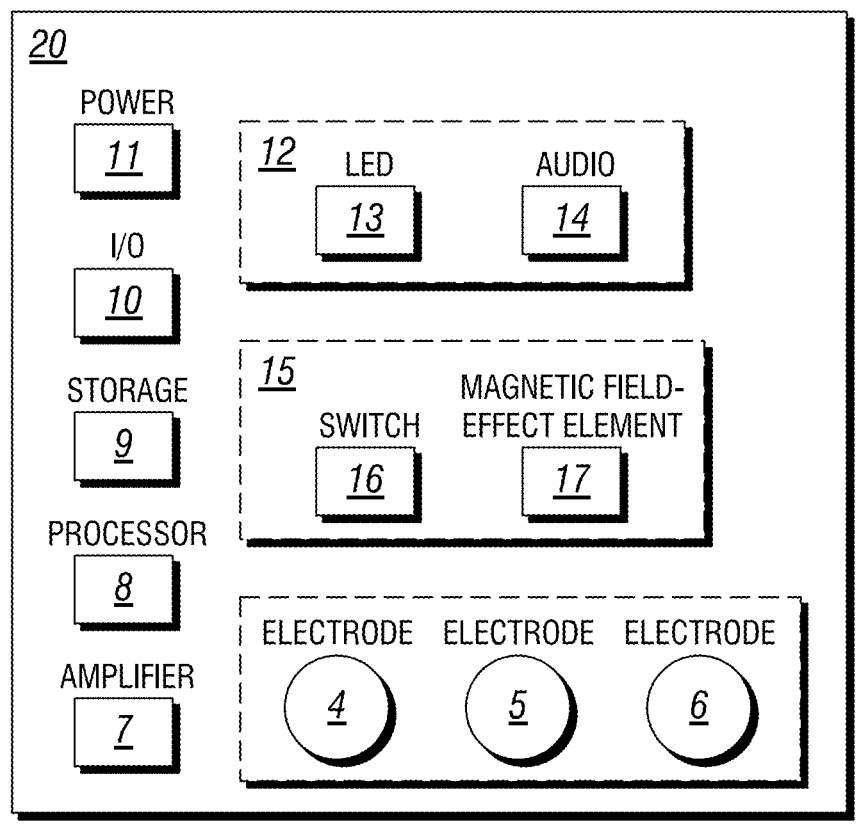
FIG. 3 is a schematic illustration of components within a self-contained EEG recording patch in accordance with the disclosure.
Figure 4:
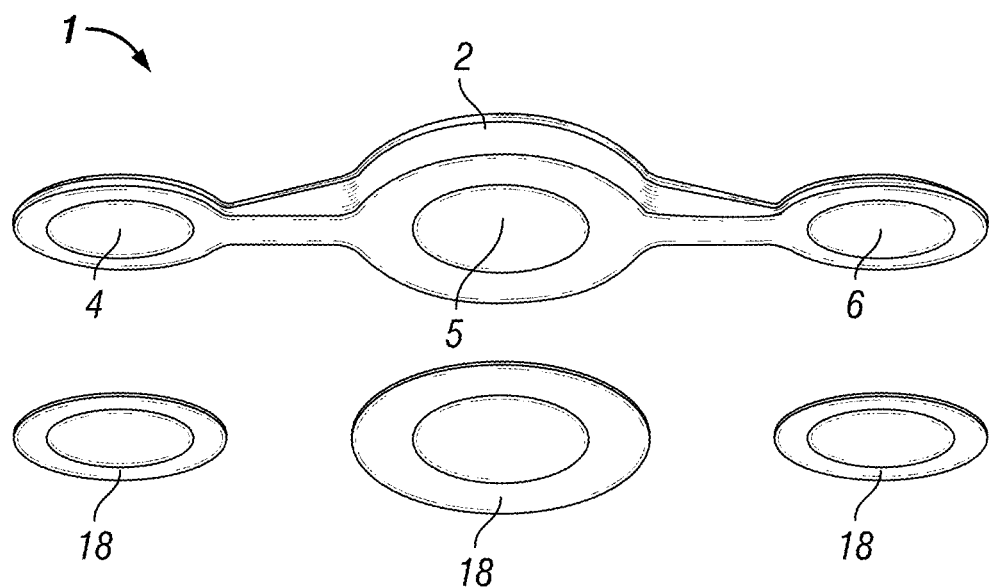
FIG. 4 is a perspective bottom view illustration of replaceable conductive hydrogels that interface between the self-contained EEG recording patch and the scalp on an embodiment of a three-electrode EEG device in accordance with the disclosure.

In another embodiment shown, for example, in FIGS. 2 & 4, the self-contained patch 1 has three electrodes 4, 5, 6 and is used as a tool to record frontal EEG below the hairline before, during, and after sleeping. The electrode 4, 5, 6, spacing is based on typical devices used to record the stages of sleep from frontal EEG. As with these typical devices, the patch 1 in this embodiment is meant to be placed below the hairline, centered with the nose where the electrodes make a parallel line with the eyes. Electrodes 4 and 6 are referenced to electrode 5.

In this embodiment, the patch 1 has the ability to be turned on and off via recording state switch 15 when needed either through a magnetic field-effect element 17 or through a switch 16 such as a membrane-type, or momentary-type switch, built into the enclosure 2 of the patch 1. For embodiments of the patch 1 using a recording state switch 15 comprising a magnetic field-effect switch 17, such as a Hall-effect sensor, the patch 1 may simply be placed in a receiver cradle, or the like, that contains a magnetic element that changes the recording state of the patch to a sleep state. Removing the patch 1 from the cradle, and subsequent removal of the magnetic field, could then cause the magnetic field effect switch 17 to change the patch 1 from a sleep state to a recording state. Likewise, in this embodiment, the self-contained patch 1 may also include a recording state indicator 12 to indicate the change in recording state from record to sleep, or from sleep to record. This indicator may be an LED element 13 that flashes to indicate the change in state. This indicator may also be, or include, an auditory indicator 14 to indicate the change in state. Other indicators, or combinations of indicators, are also possible.

Figure 5:
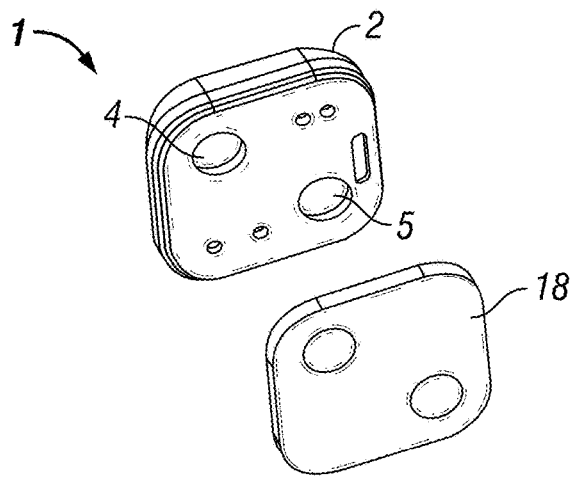
FIG. 5 is a perspective bottom view of an illustration of replaceable conductive hydrogels that interface between the self-contained EEG recording patch and the scalp on an embodiment of a two-electrode device in accordance with the disclosure.

In this embodiment, after the patch 1 is in record mode, the patch 1 is then placed on the scalp below the hairline using a conductive hydrogel 18, or the like, that also provides enough adhesion to the scalp for effective recording of EEG for up to a twelve hour period. Alternatively, the patch 1 may be adhered with a combination conductive hydrogel 18 with an adhesive construct. The EEG data itself is recorded in the standard European Data Format (EDF), or any other suitable format. After nightly use, the conductive hydrogels 18 can simply be peeled off of the patch and thrown away. Prior to the next night's use, new conductive hydrogels 18 can be applied to the patch as applying a sticker. FIG. 4 is a perspective bottom view illustration of replaceable conductive hydrogels 18 that interface between the self-contained EEG recording patch 1 and the scalp on an embodiment of a three-electrode EEG device 1. FIG. 5 is a perspective bottom view of an illustration of replaceable conductive hydrogels 18 that interface between the self-contained EEG recording patch 1 and the scalp on an embodiment of a two-electrode device. Other configurations and hydrogels 18 are also possible.

This process of recording EEG each night may be done for up to ten nights with a single patch 1. In this embodiment, the patch 1 may be used to record the different stages of sleep for multiple nights in many different environments such as in the user's home. Once ten nights of EEG have been recorded, the patch 1 may be placed in the mail to a service that reads the EEG to identify sleep stages according to AASM guidelines. In other embodiments, the data on the patch 1 may be accessed via I/O data retrieval port 10 and uploaded, or otherwise sent to a service. Sleep architecture may be identified in a report along with EEG recording attributes and made available to physicians through a user's electronic medical records, or the like. Alternatively, the raw EDF data can be made available to physicians for review.

Figure 6:
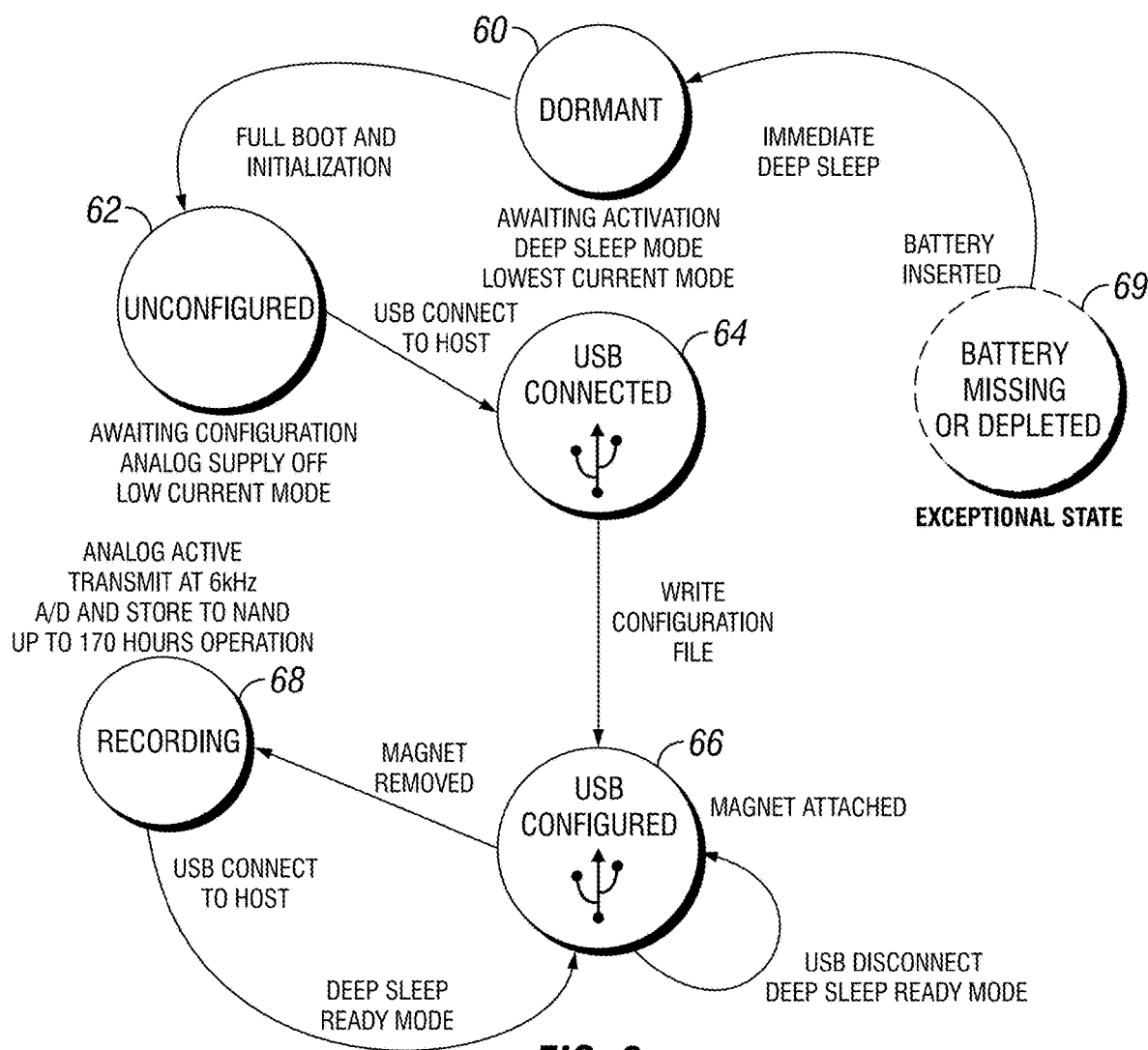
FIG. 6 is an exemplary state diagram for an embodiment of the self-contained EEG recording patch in accordance with the disclosure.

FIG. 6 is an exemplary state diagram for an embodiment of the self-contained EEG recording patch in accordance with the disclosure. As shown in FIG. 6, embodiments of the self-contained EEG recording patch 1 may have a dormant state 60 in which the patch 1 is awaiting activation in a deep sleep and lowest current mode. Upon a full boot and initialization, the patch 1 may enter an unconfigured state 62 where patch 1 is awaiting configuration with analog supply off and in a low current mode. Upon connection of a USB to a host, patch 1 may enter a USB connected state 64. Upon a configuration file being written, patch 1 may enter a USB configured state 66. While patch 1 remains USB configured (e.g., magnet attached, or device cradled, switched off, or the like) it may be in a deep sleep ready mode. Upon activation (e.g., magnet removed, or device removed from cradle, or switched on, or the like) the patch 1 may enter a recording state 68. As also indicated, patch 1 may enter an exceptional state 69 when a power source is missing, depleted, or the like.

Figure 7:
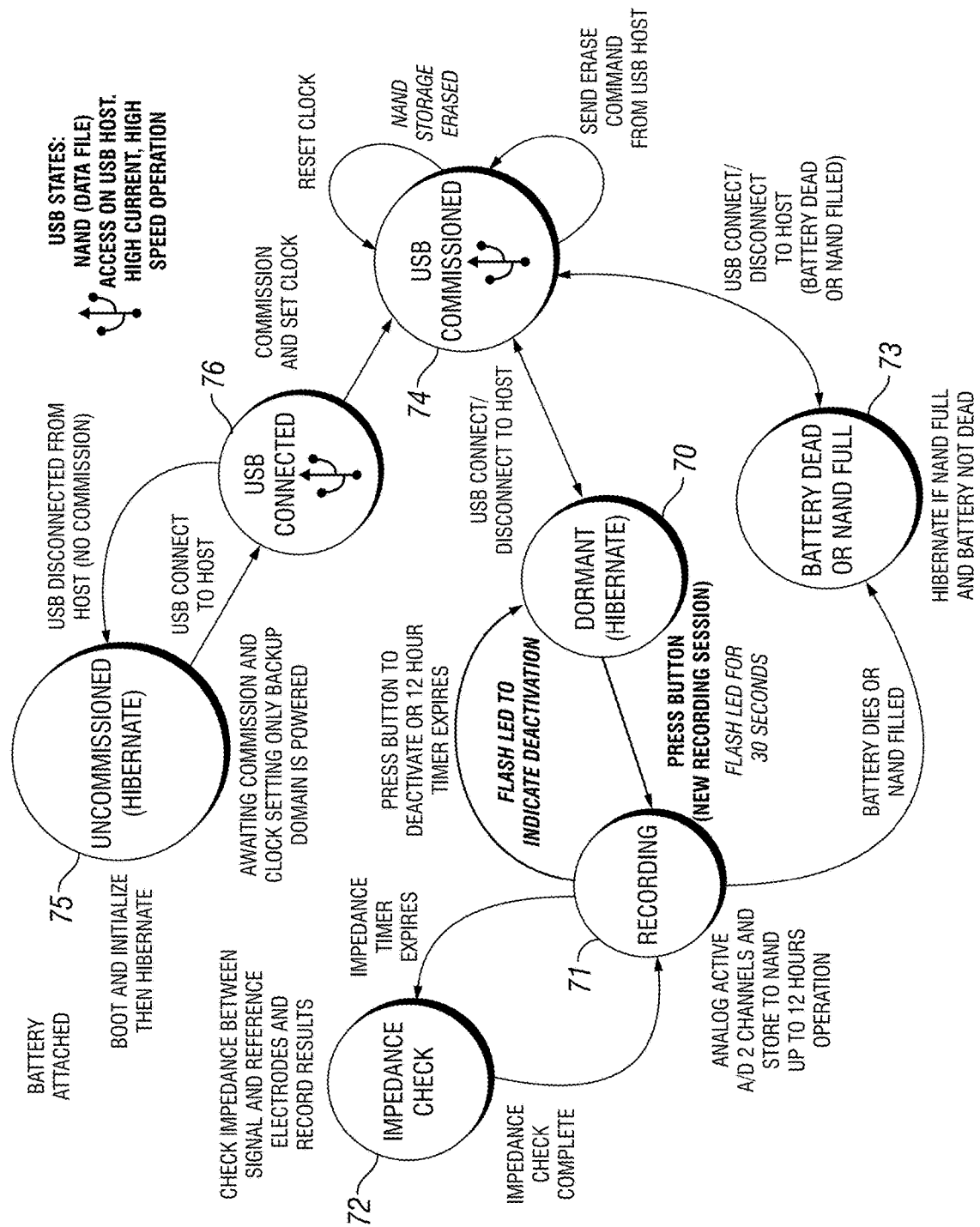
FIG. 7 is an exemplary state diagram for another embodiment of the self-contained EEG recording patch in accordance with the disclosure.

FIG. 7 is an exemplary state diagram for another embodiment of the self-contained EEG recording patch in accordance with the disclosure. As shown, embodiments of the self-contained EEG recording patch 1 may have a dormant state 70 where the device is hibernating. Upon activation (e.g., magnet removed, or device removed from cradle, or switched on, or the like) the patch 1 may enter a recording state 71. From recording state 71 the patch 1 may also enter an impedance check state 72 from which patch 1 may return to recording state 71 upon completion of the impedance check. Patch 1 may enter another power source dead state 73 if a power source dead or storage 9 is full condition is detected. The patch may also enter a USB commissioned state 74 when a USB connect condition is detected. Initially, a patch 1 may be in an uncommissioned state 75 until connected to a host via USB, or the like, when it enters a USB connected state 76. Other conditions for entering the various states are also indicated on FIGS. 6-7.

Figure 8:
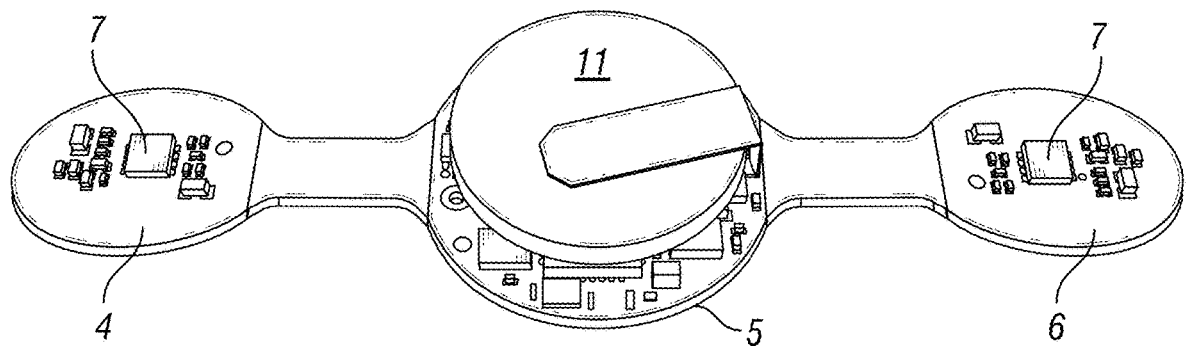
FIG. 8 is an electronic circuit layout illustration for an embodiment of the self-contained EEG recording patch in accordance with the disclosure showing components and power source with the patch enclosure removed.

FIG. 8 is an electronic circuit layout illustration for an embodiment of the self-contained EEG recording patch in accordance with the disclosure showing components and power source 11 (e.g., a battery, capacitor, or the like) with the patch enclosure 2 removed. As also shown, each electrode 4, 5, 6 may have amplification circuitry 7 as disclosed herein.

Figure 9:
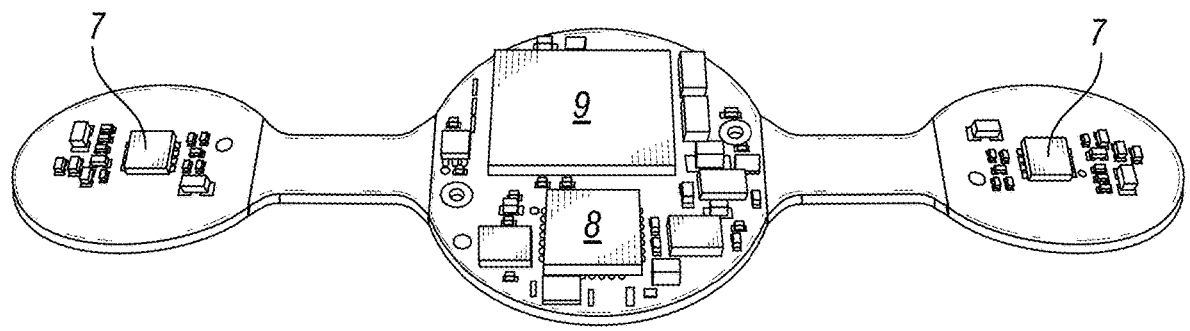
FIG. 9 is an electronic circuit layout illustration for an embodiment of the self-contained EEG recording patch in accordance with the disclosure showing components without the power source and without the patch enclosure.

FIG. 9 is an electronic circuit layout illustration for an embodiment of the self-contained EEG recording patch in accordance with the disclosure showing components without the power source 11 (e.g., battery, capacitor, or the like) and without the patch enclosure 2. In some embodiments, as shown, storage 9 and data processor 8 may be located in the space under power source 11.

Figure 10:
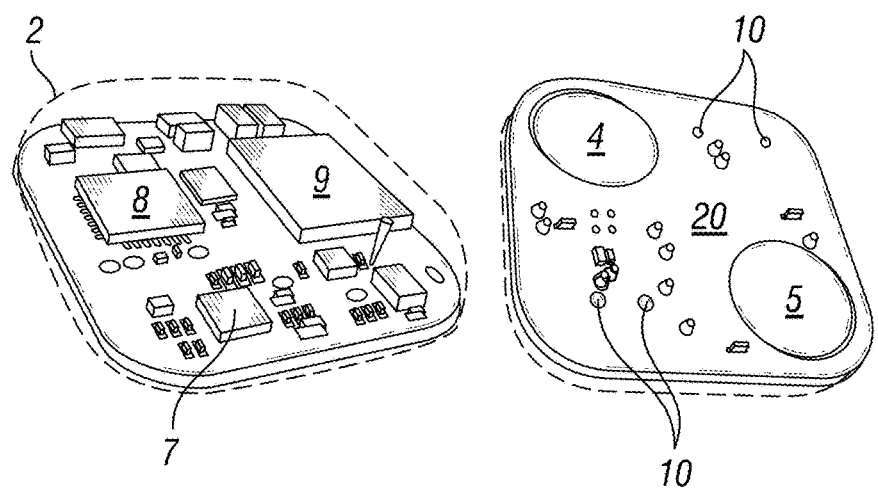
FIG. 10 is an electronic circuit layout illustration for the top and bottom sides of an embodiment of the self-contained EEG recording patch showing components in another layout in accordance with the disclosure.

FIG. 10 is an electronic circuit layout illustration for the top (left side of FIG. 10) and bottom (right side of FIG. 10) sides of an embodiment of the self-contained EEG recording patch 1 showing components in another layout in accordance with the disclosure without the power source 11 (e.g., battery, capacitor, or the like) or over-mold enclosure 2 on the top. The electrodes 4, 5, programming pads, 10, and I/O programming pads 10 are visible on the bottom side of the patch 1. The top side of the patch may house the amplification circuitry 7, data processor 8, and storage 9 as shown.

Figure 11:
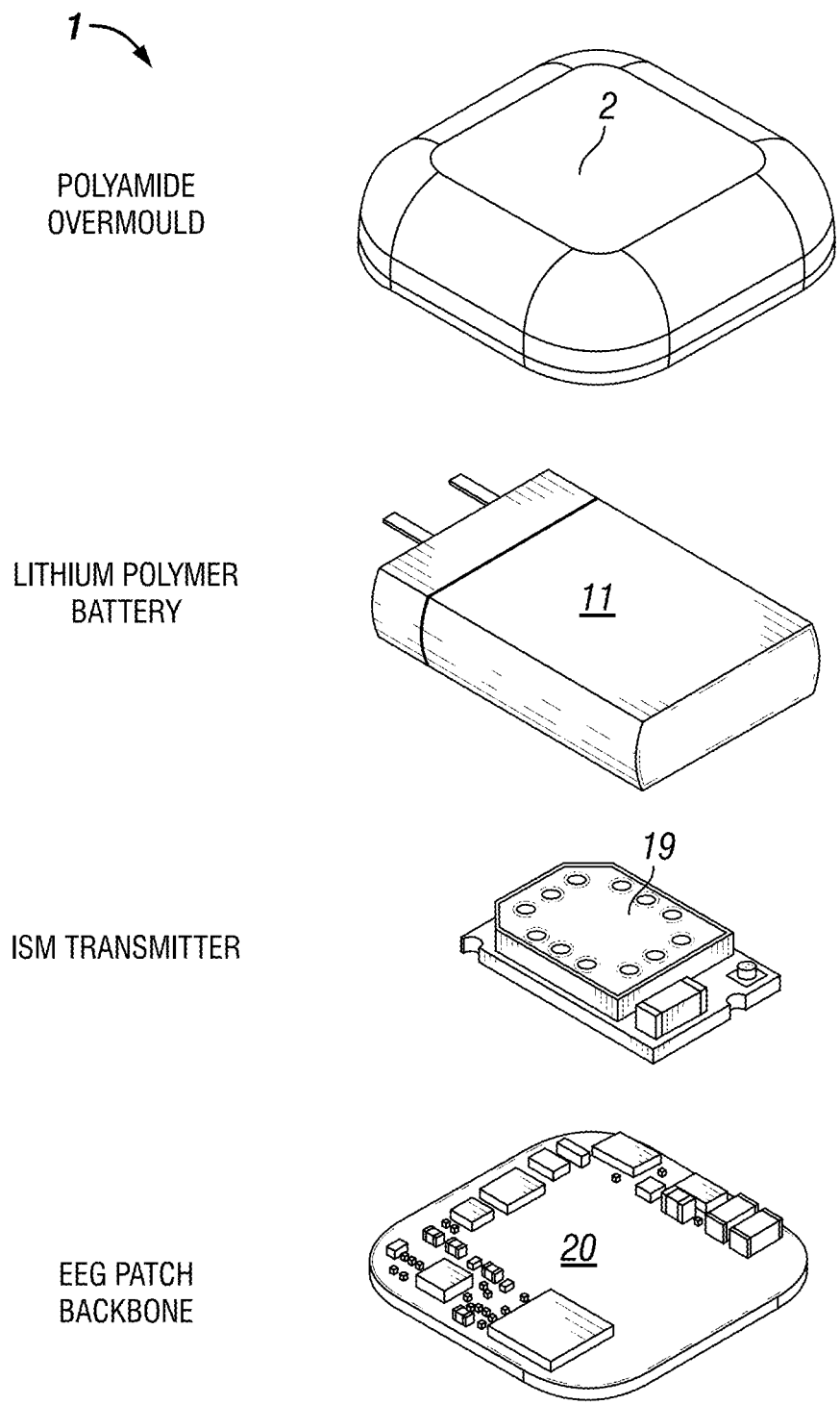
FIG. 11 is an exploded perspective view of an electronic circuit layout illustration for an embodiment of the self-contained EEG recording patch in accordance with the disclosure showing the enclosure overmolding, power source, transmitter and circuit backbone.

FIG. 11 is an exploded perspective view of an electronic circuit layout illustration for an embodiment of the self-contained EEG recording patch 1 in accordance with the disclosure showing the enclosure 2 overmolding, power source 11, transmitter 19 and circuit board substrate 20. Other configurations are also possible.

Figure 12:
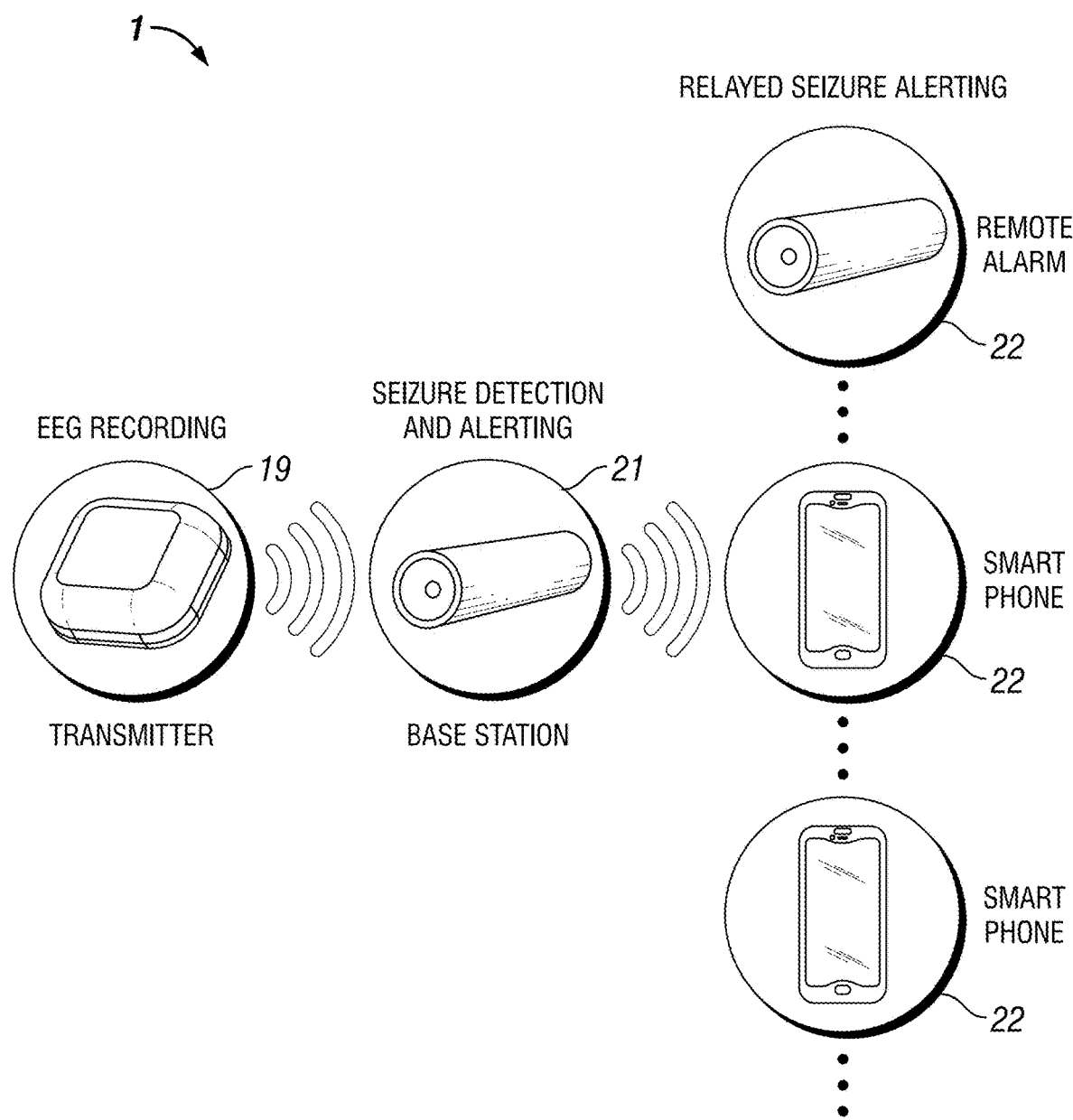
FIG. 12 is a schematic illustration of an embodiment of the self-contained EEG recording device as a seizure alerting method in accordance with the disclosure whereby the transmitter attached to the scalp transmits EEG in real-time to a base station that analyzes the EEG for seizures and stores the EEG for later retrieval.

FIG. 12 is a schematic illustrating an embodiment of the self-contained EEG recording patch 1 as a seizure alerting method in accordance with the disclosure whereby the transmitter 19 in the patch 1 attached to the scalp transmits EEG in real-time to a base station 21 that analyzes the EEG for seizures and stores the EEG for later retrieval. Once a seizure is detected the base station 21 can alert to the seizure and/or relay the alert to other devices 22 such as a smart phone, alarm, or the like.

Figure 13:
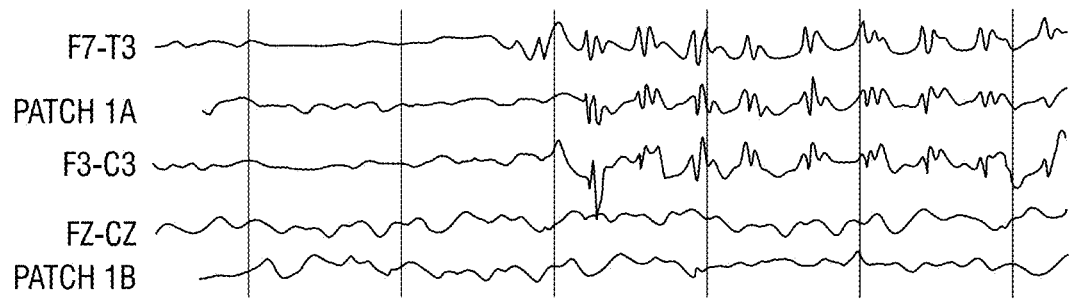
FIG. 13 is a schematic illustration demonstrating the concept of single-channel seizure detection based on scalp location in accordance with the disclosure.
Figure 13:
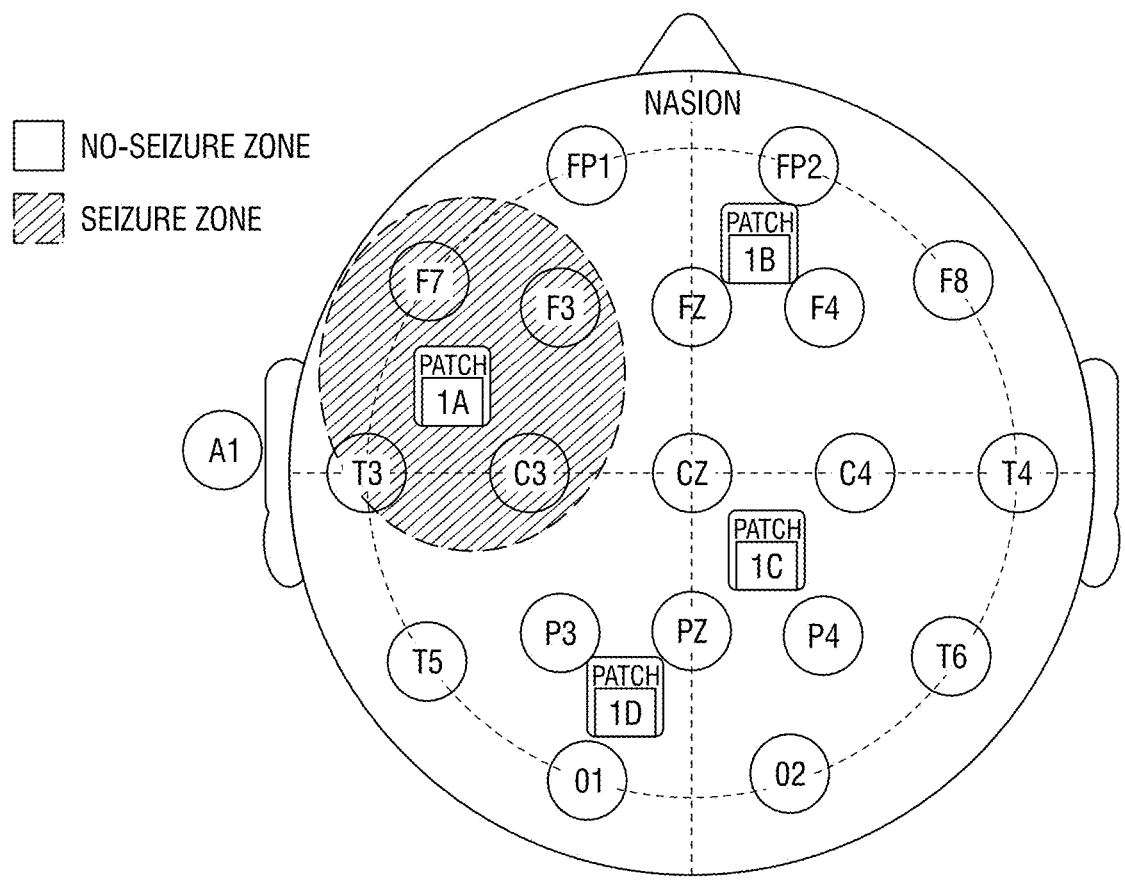

FIG. 13 is a schematic illustration demonstrating the concept of single-channel seizure detection based on scalp location in accordance with the disclosure. In this schematized example, an embodiment of the patch 1 fits between any two electrodes (e.g., F7-F8, Fp1-Fp2, T3-T6, O1-O2, F3-F4, P3-P4, C3-C4, Fz, Cz, and Pz) in the typical wired EEG. For example, a seizure is recorded by the F7-T3 and F3-C3 wired electrode pairs. Likewise EEG Patch 1a, located between these wired pairs, will also record spike-wave discharges, whereas wired pair Fz-Cz and EEG Patches 1b-1d, do not record seizure activity demonstrating the potential for scalp-specific locations for seizure detection.

Figure 14:
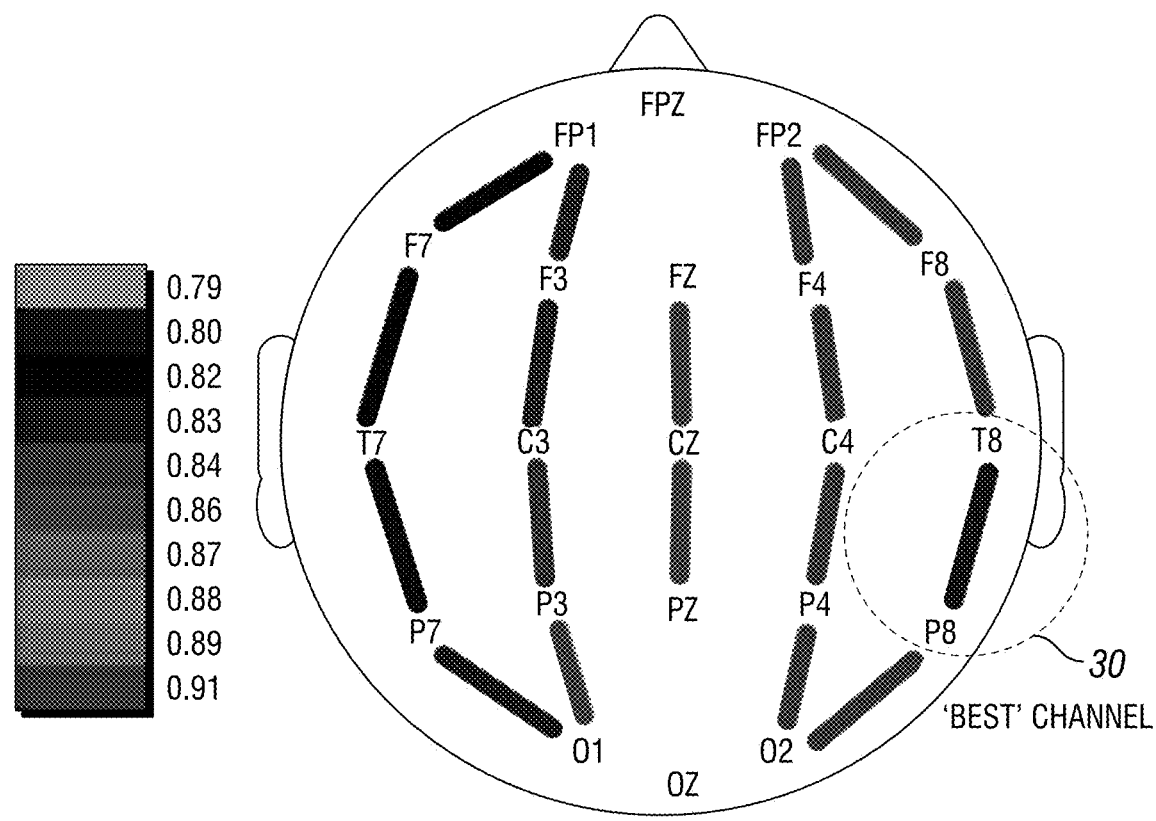
FIG. 14 is a schematic illustration of a map of the scalp showing an example of single channel seizure detection performance as a probability map for an individual person based on standard EEG electrode locations in accordance with the disclosure.

FIG. 14 is a schematic illustration of a map of the scalp showing an example of single channel seizure detection performance as a probability map for an individual person based on standard EEG electrode locations in accordance with the disclosure. In this example there is a 'best channel' 30 that has the highest probability for detecting future seizures in this particular person. These maps may be generated for each person's seizure signature to identify the best scalp location to place the patch 1 to reliably detect seizure activity.

Figure 15:
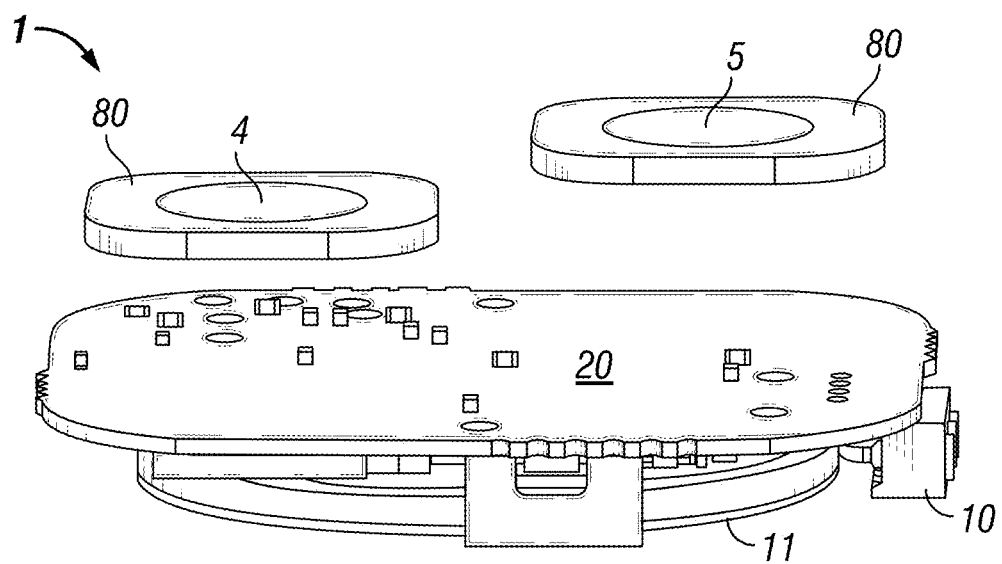
FIG. 15 is an exploded perspective view of the electronic circuit layout illustration for the bottom of an embodiment of the self-contained EEG recording patch in accordance with the disclosure showing components, data I/O, dais boards off of the substrate, and power source with the patch enclosure removed.

FIG. 15 is an exploded perspective view of the electronic circuit layout illustration for the bottom of an embodiment of the self-contained EEG recording patch 1 in accordance with the disclosure showing components, I/O programming and retrieval 10, dais boards 80 off of the substrate 20, containing electrodes 4, 5, and power source 11, with the patch enclosure 2 removed. Other configurations are also possible.

Figure 16:
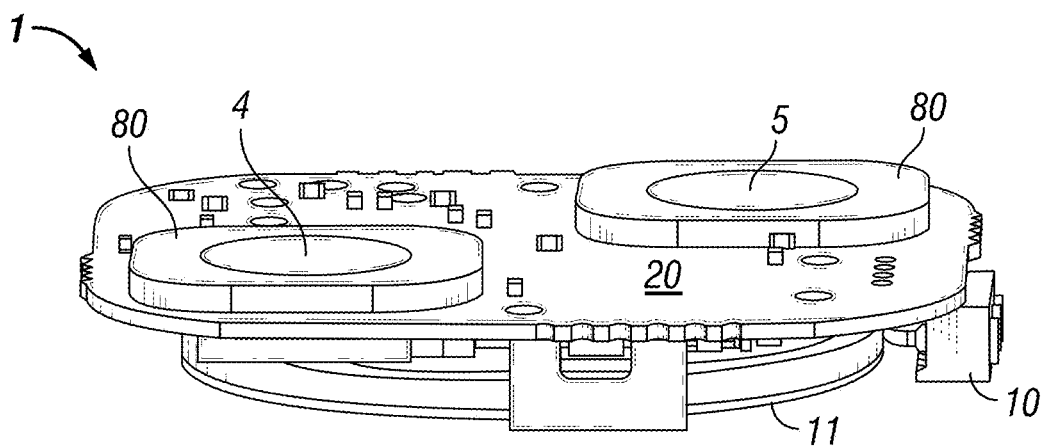
FIG. 16 is an electronic circuit layout illustration for the bottom of an embodiment of the self-contained EEG recording patch in accordance with the disclosure showing components, data I/O, dais boards surface-mounted to the substrate, and power source with the patch enclosure removed.

FIG. 16 is an electronic circuit layout illustration for the bottom of an embodiment of the self-contained EEG recording patch 1 in accordance with the disclosure showing components, I/O programming and data retrieval 10, dais boards 80 surface-mounted to the substrate 20, with electrodes 4, 5, and power source 11 with the patch enclosure 2 removed. Other configurations are also possible.

Another embodiment of the "dais assembly" construction described above uses standard immersion silver as the electrode 4, 5, 6 surface finish. The dais boards 80 are then masked to expose only the electrode 4, 5, 6, metal surface using known printed circuit board lithography techniques, and placed in a bath containing sodium hypochlorite solution to develop a silver chloride layer on the surface of the silver electrode 4, 5, 6. This method leverages known printed circuit board fabrication techniques and equipment to fabricate an Ag—AgCl biopotential electrode. The finished dais boards 80 are then attached to the main circuit board or substrate 20 as described above.

In another embodiment shown, for example, in FIGS. 17, 18, 19 & 20, the self-contained EEG recording patch 1 has two memory shape alloy electrodes 90 that are used to mechanically fix the patch 1 to a patient's scalp. Plungers 91, are used to inject the memory shape alloy electrodes 90 into the scalp. The memory shape alloy electrodes 90, facilitate low-impedance connections between the patch 1 and the scalp for recording biopotentials.

Figure 17:
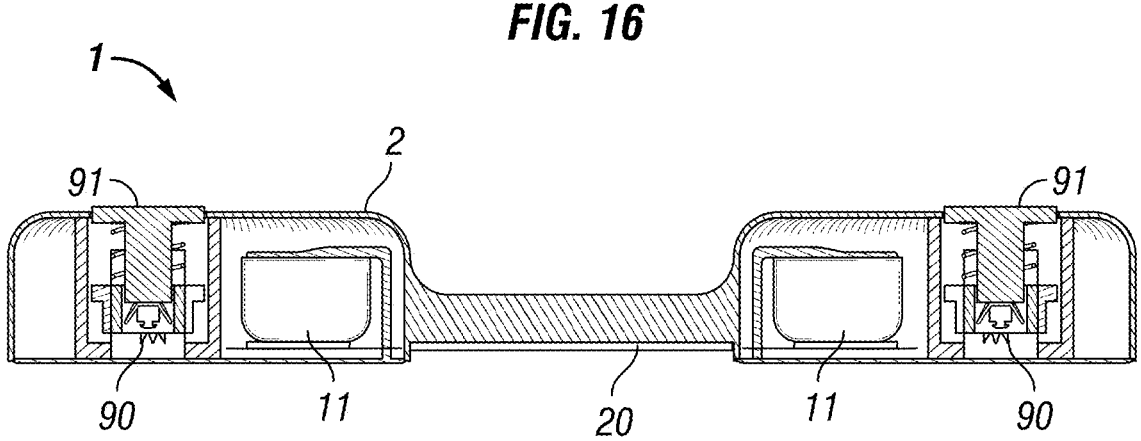
FIG. 17 is a sectioned view of the electronic circuit layout illustration for the bottom of an embodiment of the self-contained EEG recording patch in accordance with the disclosure showing components, memory shape alloy electrodes in their storage state, the plungers used to inject the memory shape alloy electrodes into the scalp, and power source with the patch enclosure.

FIG. 17 is a sectioned view of the electronic circuit layout illustration for the bottom of an embodiment of the self-contained EEG recording patch 1 in accordance with the disclosure showing components, memory shape alloy electrodes 90 in their storage state, the plungers 91, used to inject the memory shape alloy electrodes into the scalp for mechanical fixation to the scalp, and power source 11 with the patch enclosure 2. Other configurations are also possible.

Figure 18:
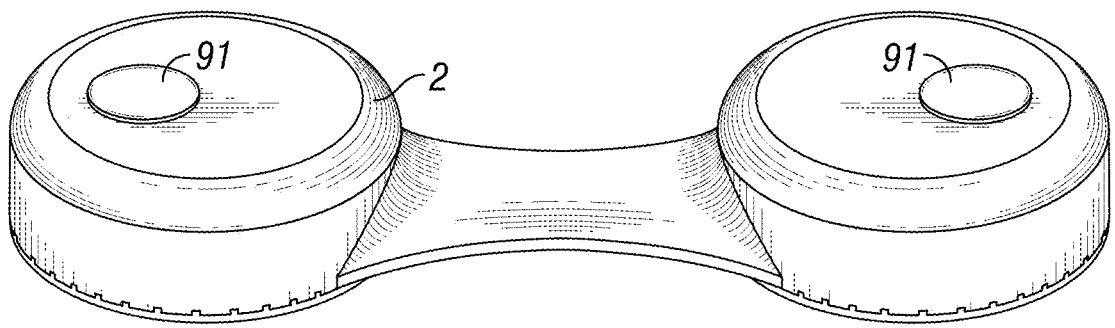
FIG. 18 is a top perspective view of an embodiment of the self-contained EEG recording patch in accordance with the disclosure showing the plungers with the patch enclosure.

FIG. 18 is a top perspective view of an embodiment of the self-contained EEG recording patch 1 in accordance with the disclosure showing the plungers 91 with the patch enclosure 2. Other configurations are also possible.

Figure 19:
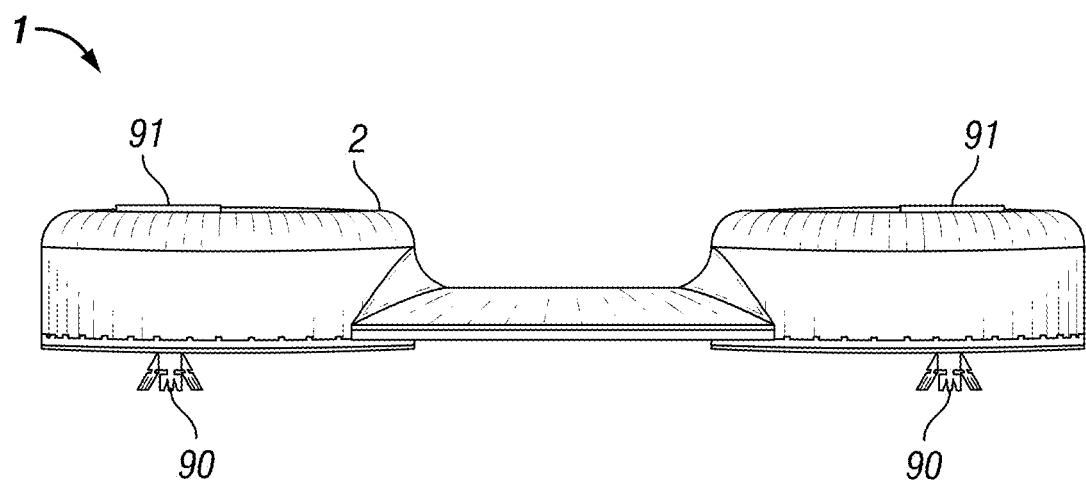
FIG. 19 is a side view of an embodiment of the self-contained EEG recording patch in accordance with the disclosure showing memory shape alloy electrodes in their deployed state but not yet retaining their memory shape, and the plungers used to inject the memory shape alloy electrodes into the scalp with the patch enclosure.

FIG. 19 is a side view of an embodiment of the self-contained EEG recording patch 1 in accordance with the disclosure in accordance with the disclosure showing memory shape alloy electrodes 90 in their deployed state, but not yet retaining their memory shape, and the plungers 91 used to inject the memory shape alloy electrodes into the scalp with the patch enclosure 2. Other configurations are also possible.

Figure 20:
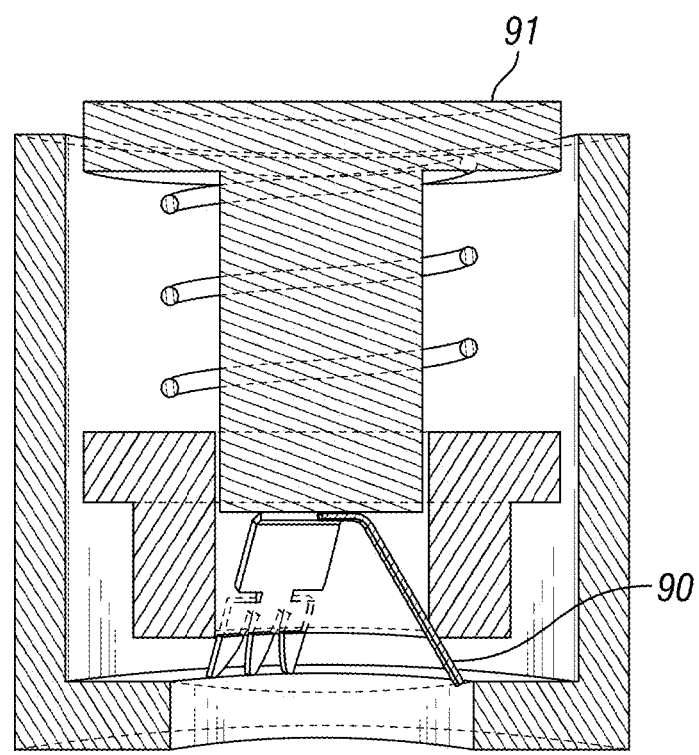
FIG. 20 is a sectioned view of the memory shape alloy mechanism in its storage state with plunger.

FIG. 20 is a sectioned view of the memory shape alloy 90 mechanism in its storage state with plunger 91. Other configurations are also possible.

Although various embodiments have been shown and described, the present disclosure is not so limited and will be understood to include all such modifications and variations are would be apparent to one skilled in the art.

What is claimed is:

1. A self-contained electroencephalogram (EEG) recording patch adapted to be worn by a user, comprising:
    a patch housing that encloses:
        a substrate having a power source; a single pair of measuring electrodes; a memory; and circuitry disposed thereon;
        an I/O port that provides a physical interface for communication between the memory and an external device;
        the patch housing including a surface having apertures for the single pair of measuring electrodes and the I/O port; and
    a sticker including hydrogel adapted to reversibly attach to the surface of the patch housing and reversibly attach the patch to a scalp of the user;
    wherein:
        in an attached condition, the sticker completely covers the I/O port; and
        in a detached condition, the sticker is removed from the surface of the patch housing;
        the circuitry, after activation of the patch, is configured to use the power source to enter the patch into a disconnected, continuous recording state for recording, using the single pair of measuring electrodes, EEG data into the memory for a time period lasting at least 12 hours, wherein:
            in the disconnected, continuous recording state, the patch is in the attached condition and the EEG data is not transmitted to the external device; and
            in a connected, non-recording state, the patch is in the detached condition and the circuitry is configured to communicate the EEG data to the external device using the I/O port.
2. The patch of claim 1, comprising a plurality of replaceable stickers adapted to reversibly attach to the surface.
3. The patch of claim 1, wherein the patch does not include a wireless communication mechanism.
4. The patch of claim 1, wherein the time period lasts up to 170 hours.
5. The patch of claim 1, wherein the circuitry performs an impedance check, using the single pair of measuring electrodes, prior to entering into the disconnected, continuous recording state.

* * * * *

UNITED STATES PATENT AND TRADEMARK OFFICE
CERTIFICATE OF CORRECTION

PATENT NO. : 11,020,035 B2  
APPLICATION NO. : 15/421085  
DATED : June 1, 2021  
INVENTOR(S) : Francis E. Dudek et al.

Page 1 of 1

It is certified that error appears in the above-identified patent and that said Letters Patent is hereby corrected as shown below:

In the Specification

On Column 1, Line 12, before the "FIELD OF DISCLOSURE" section, please insert the following paragraph:
-- STATEMENT REGARDING FEDERALLY SPONSORED RESEARCH OR DEVELOPMENT
This invention was made with government support under grant number R43 NS100235 awarded by the National Institutes of Health. The government has certain rights in the invention. --

Signed and Sealed this
First Day of February, 2022

Drew Hirshfeld
*Performing the Functions and Duties of the
Under Secretary of Commerce for Intellectual Property and
Director of the United States Patent and Trademark Office*

UNITED STATES PATENT AND TRADEMARK OFFICE
CERTIFICATE OF CORRECTION

PATENT NO. : 11,020,035 B2  
APPLICATION NO. : 15/421085  
DATED : June 1, 2021  
INVENTOR(S) : Francis E. Dudek Page 1 of 1

It is certified that error appears in the above-identified patent and that said Letters Patent is hereby corrected as shown below:

In the Specification

Column 1, Line 12, after "reference herein." please insert a return followed by the heading --STATEMENT REGARDING FEDERALLY SPONSORED RESEARCH OR DEVELOPMENT-- followed by a return, and on the next line please insert --This invention was made with Government support under grant number R43 NS100235 awarded by the National Institutes of Health. The Government has certain rights in the invention.-- followed by a return.

This certificate supersedes the Certificate of Correction issued February 1, 2022.

Signed and Sealed this  
Eighth Day of October, 2024

Katherine Kelly Vidal  
*Director of the United States Patent and Trademark Office*